US011708339B2

(12) United States Patent
Hoyt et al.

(10) Patent No.: US 11,708,339 B2
(45) Date of Patent: Jul. 25, 2023

(54) BIODERIVED BENZOXAZINES

(71) Applicant: Alliance for Sustainable Energy, LLC, Golden, CO (US)

(72) Inventors: Caroline Bradshaw Hoyt, Denver, CO (US); Gregg Tyler Beckham, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/690,131

(22) Filed: Mar. 9, 2022

(65) Prior Publication Data

US 2022/0289695 A1 Sep. 15, 2022

Related U.S. Application Data

(60) Provisional application No. 63/158,416, filed on Mar. 9, 2021.

(51) Int. Cl.
*C07D 263/58* (2006.01)
*C07D 413/10* (2006.01)
*C07D 263/57* (2006.01)

(52) U.S. Cl.
CPC ......... *C07D 263/58* (2013.01); *C07D 263/57* (2013.01); *C07D 413/10* (2013.01)

(58) Field of Classification Search
CPC .............................. C07C 39/14; C07D 263/58
See application file for complete search history.

(56) References Cited

PUBLICATIONS

Akubue et al Egyptian Journal of Pharmaceutical Sciences, 1991, vol. 32(1-2), p. 325-330 (CAS Abstract Only).*
Agag, "Preparation and properties of some thermosets derived from allyl-functional naphthoxazines", Journal of Applied Polymer Science, 2006, vol. 100, pp. 3769-3777.
Agag et al., "Benzoxazole Resin: A Novel Class of Thermoset Polymer via Smart Benzoxazine Resin", Macromolecules, 2012, vol. 45, No. 22, pp. 8991-8997.
Andreu et al., "Carboxylic Acid-Containing Benzoxazines as Efficient Catalysts in the Thermal Polymerization of Benzoxazines", Journal of Polymer Science: Part A: Polymer Chemistry, 2008, vol. 46, pp. 6091-6101.
Andreu et al., "Studies on the Thermal Polymerization of Substituted Benzoxazine Monomers: Electronic Effects", Journal of Polymer Science: Part A: Polymer Chemistry, 2008, vol. 46, pp. 3353-3366.
Arza et al., "Design, Synthesis, Characterization, and Polymerization of Fused-Ring Naphthoxazine Resins", Macromolecules, 2017, vol. 50, pp. 9249-9256.
Baqar et al., "Polymerization behavior of methylol-functional benzoxazine monomer", Reactive and Functional Polymers, 2013, vol. 73, No. 2, pp. 360-368.

Dong et al., "Effect of N-substituents on the surface characteristics and hydrogen bonding network of polybenzoxazines". Polymer, Feb. 2011, vol. 52, No. 4, pp. 1092-1101.
Dunkers et al., "Reaction of Benzoxazine-Based Phenolic Resins with Strong and Weak Carboxylic Acids and Phenols as Catalysts", Journal of Polymer Science: Part A: Polymer Chemistry, 1999, vol. 37, pp. 1913-1921.
Goto et al., "Synthesis and Cross-Linking of a Benzoxazine-ContainingAnthracene Moiety: Thermally Stable PhotoluminescentBenzoxazine Resin", Macromolecules, 2020, vol. 53, p. 6640-6648.
Goydan et al., "Estimation of the Solubilities of Organic Compounds in Polymers by Group-Contribution Methods", Industrial & Engineering Chemistry Research, 1989, vol. 28, pp. 445-454.

(Continued)

*Primary Examiner* — Kamal A Saeed
(74) *Attorney, Agent, or Firm* — Michael A. McIntyre

(57) ABSTRACT

The present disclosure relates to a composition having a structure that includes

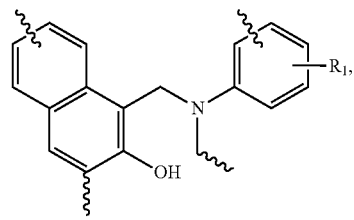

where $R_1$ includes at least one of hydrogen, carbon, and/or fluorine, and ⌇ includes a covalent bond. In some embodiments of the present disclosure, $R_1$ may include at least one of hydrogen, fluorine, a carboxyl group, a hydroxyl group, an alkoxy group, and/or a hydrocarbon chain. In some embodiments of the present disclosure, the composition may be derived from at least one of

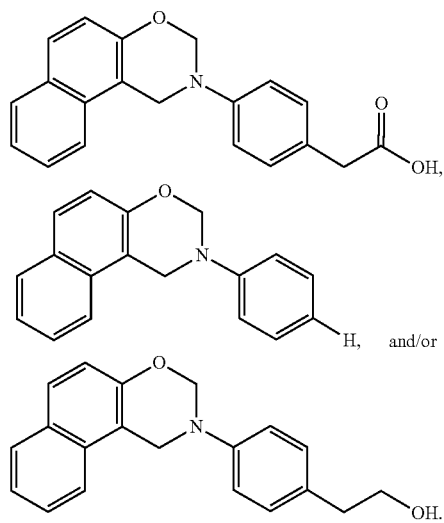

In some embodiments of the present disclosure, at least a portion of the composition may be bioderived.

4 Claims, 13 Drawing Sheets

(56) References Cited

PUBLICATIONS

Ishida et al., "Catalyzing the curing reaction of a new benzoxazine-based phenolic resin", Journal of Applied Polymer Science, 1995, vol. 58, pp. 1751-1760.

Ishida et al., "A study on the volumetric expansion of benzoxazine-based phenolic resin", Macromolecules, 1997, vol. 30, pp. 1099-1106.

Kim et al., "Synthesis and thermal characterization of polybenzoxazines based on acetylene-functional monomers", Polymer, 1999, vol. 40, pp. 6565-6573.

Kiskan et al., "Synthesis and Characterization of Fluid 1,3-Benzoxazine Monomers and Their Thermally Activated Curing", Journal of Polymer Science: Part A: Polymer Chemistry, 2009, vol. 47, pp. 6955-6961.

Kudoh et al., "A Highly Reactive Benzoxazine Monomer, 1-(2 Hydroxyethyl)-1,3-Benzoxazine: Activation of Benzoxazine by Neighboring Group Participation of Hydroxyl Group", Macromolecules, 2010, vol. 43, pp. 1185-1187.

Kuo et al., "Preparing low-surface-energy polymer materials by minimizing intermolecular hydrogen-bonding interactions", The Journal of Physical Chemistry C, 2009, vol. 113, pp. 20666-20673.

Li et al., "Investigation of polybenzoxazine gelation using laser light scattering", Journal of Applied Polymer Science, 2018, 45709, pp. 3-5.

Liu et al., "Enhanced Thermal Property and Flame Retardancy via Intramolecular 5-Membered Ring Hydrogen Bond-Forming Amide Functional Benzoxazine Resins", Macromolecules, 2018, vol. 51, No. 23, pp. 9982-9991.

Masuo et al., "Bacterial fermentation platform for producing artificial aromatic amines", Sci. Rep., 2016, vol. 6, No. 25764, pp. 1-9.

Ohashi et al., "Synthesis and Characterization of Cyanate Ester Functional Benzoxazine and Its Polymer", Macromolecules, 2015, vol. 48, No. 23, pp. 8412-8417.

Shen et al., "Synthesis and characterization of polyfunctional naphthoxazines and related polymers", Journal of Applied Polymer Science, 1996, vol. 61, No. 9, pp. 1595-1605.

Swanepoel et al., "A Semiempirical Method for the Estimation of High-Pressure(Solvent + Polymer) Phase Boundaries in the Solution Polymerization Process", Industrial & Engineering Chemistry Research, 2021, vol. 60, pp. 697-718.

Thubsuang et al., "Facile preparation of polybenzoxazine-based carbon microspheres with nitrogen functionalities: effects of mixed solvents on pore structure and supercapacitive performance", Frontiers of Chemical Science and Engineering, 2020, vol. 14, No. 6, pp. 1072-1086.

Uyar et al., "Synthesis, characterization, and thermal properties of alkyl-functional naphthoxazines", Journal of Applied Polymer Science, 2013, vol. 127, pp. 3114-3123.

Wang et al., "Low-surface-free-energy materials based on polybenzoxazines", Angew. Chemie—International Edition, 2006, vol. 45, pp. 2248-2251.

Xu et al., "Study on the catalytic prepolymerization of an acetylene-functional benzoxazine and the thermal degradation of its cured product", RSC Advances, 2015, vol. 5, pp. 82429-82437.

Zhang et al., "Synthesis of high thermal stability polybenzoxazoles via ortho-imide-functional benzoxazine monomers", Journal of Polymer Science, Part A: Polymer Chemistry, 2015, vol. 53, pp. 1330-1338.

Zhang et al., "An anomalous trade-off effect on the properties of smart ortho-functional benzoxazines", Polymer Chemistry, 2015, vol. 6, pp. 2541-2550.

Zhang et al., "Latent Catalyst-Containing Naphthoxazine: Synthesis and Effects on Ring-Opening Polymerization", Macromolecules, 2016, vol. 49, pp. 7129-7140.

Zhang et al., "Catalyst-Free and Low-Temperature Terpolymerization in a Single-Component Benzoxazine Resin Containing Both Norbornene and Acetylene Functionalities", Macromolecules, 2018, vol. 51, No. 16, pp. 6524-6533.

Zhang et al., "Smart and sustainable design of latent catalystcontaining benzoxazine-bio-resins and application studies", Green Chemistry, 2020, vol. 22, pp. 1209-1219.

* cited by examiner

BIODERIVED BENZOXAZINES

This application claims priority from U.S. Provisional Patent Application No. 63/158,416 filed on Mar. 9, 2021, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Currently, there is the need for the bioderived replacement of petroleum-derived molecules, including amines. Among other molecules, sugars provide one possible route to achieving that goal. In addition, current technologies are constantly looking for decreased energetics for processing and petroleum-derived molecules can pose significant health problems. For example, petroleum derived materials that rely heavily on BPA for the phenolic component have been linked to negative health impacts. To date, bioderived amines are scarce. However, they could potentially relieve the burden on synthetic chemistries needed to impart amino functionality on various materials as well as reduction in greenhouse gas emissions associated with petroleum amine production. Thus, there remains a need for new chemical routes that enable the synthesis of bioderived amines suitable for replacing existing petroleum-derived molecules.

SUMMARY

An aspect of the present disclosure is a composition having a structure that includes

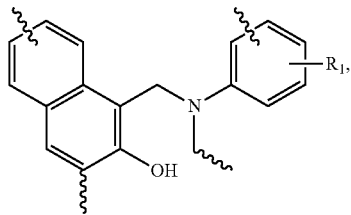

where $R_1$ includes at least one of hydrogen, carbon, and/or fluorine, and ⁓ includes a covalent bond. In some embodiments of the present disclosure, $R_1$ may include at least one of hydrogen, fluorine, a carboxyl group, a hydroxyl group, an alkoxy group, and/or a hydrocarbon chain. In some embodiments of the present disclosure, the composition may be derived from at least one of

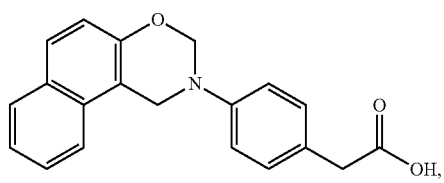

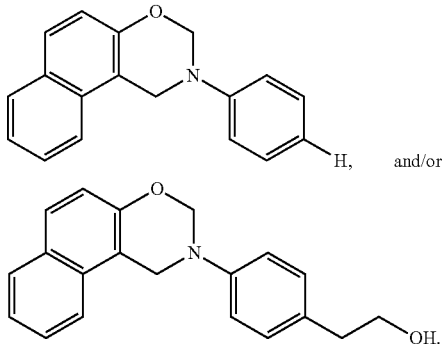

In some embodiments of the present disclosure, at least a portion of the composition may be bioderived.

An aspect of the present disclosure is a composition having a structure that includes

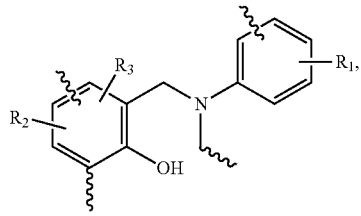

where each of $R_1$, $R_2$, and/or $R_3$ includes at least one of hydrogen, carbon, and/or fluorine, and ⁓ includes a covalent bond. In some embodiments of the present disclosure, $R_1$ may include at least one of hydrogen, fluorine, a carboxyl group, a hydroxyl group, an alkoxy group, and/or a hydrocarbon chain. In some embodiments of the present disclosure, $R_2$ may include at least one of hydrogen, fluorine, a carboxyl group, a hydroxyl group, an alkoxy group, and/or a hydrocarbon chain. In some embodiments of the present disclosure, $R_3$ may include at least one of hydrogen, fluorine, a carboxyl group, a hydroxyl group, an alkoxy group, and/or a hydrocarbon chain. In some embodiments of the present disclosure, the composition may be derived from at least one of

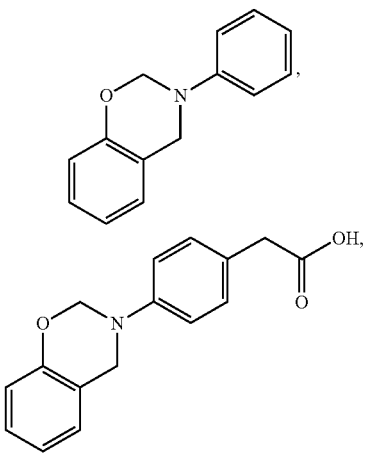

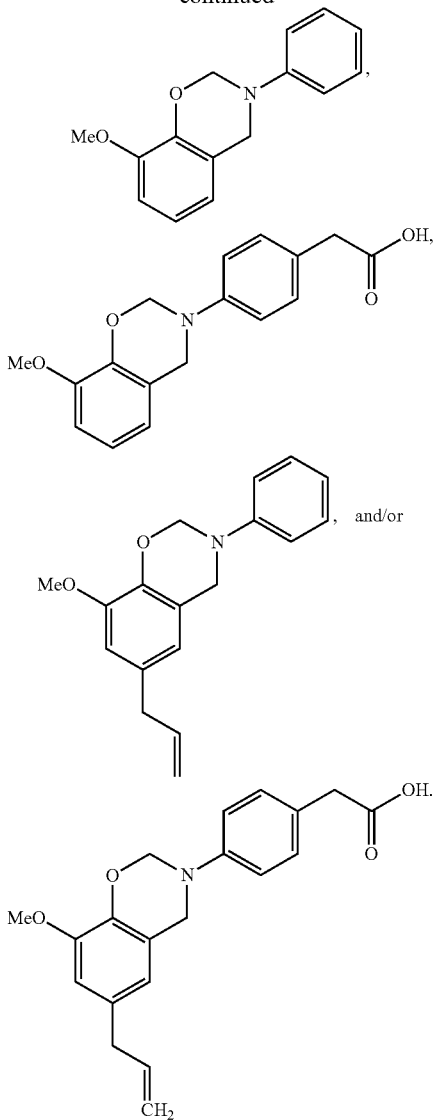

In some embodiments of the present disclosure, at least a portion of the composition may be bioderived.

An aspect of the present disclosure is a composition having a structure that includes

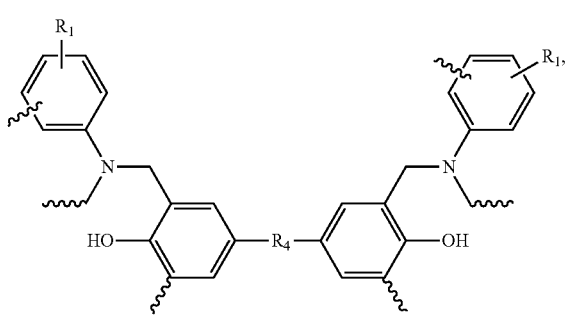

where $R_1$ includes at least one of hydrogen, carbon, and/or fluorine, $R_4$ includes at least one of a carbon, hydrogen, and/or sulfur, and ⁓ includes a covalent bond. In some embodiments of the present disclosure, $R_1$ may include at least one of hydrogen, fluorine, a carboxyl group, a hydroxyl group, an alkoxy group, and/or a hydrocarbon chain. In some embodiments of the present disclosure, the composition may be derived from at least one of

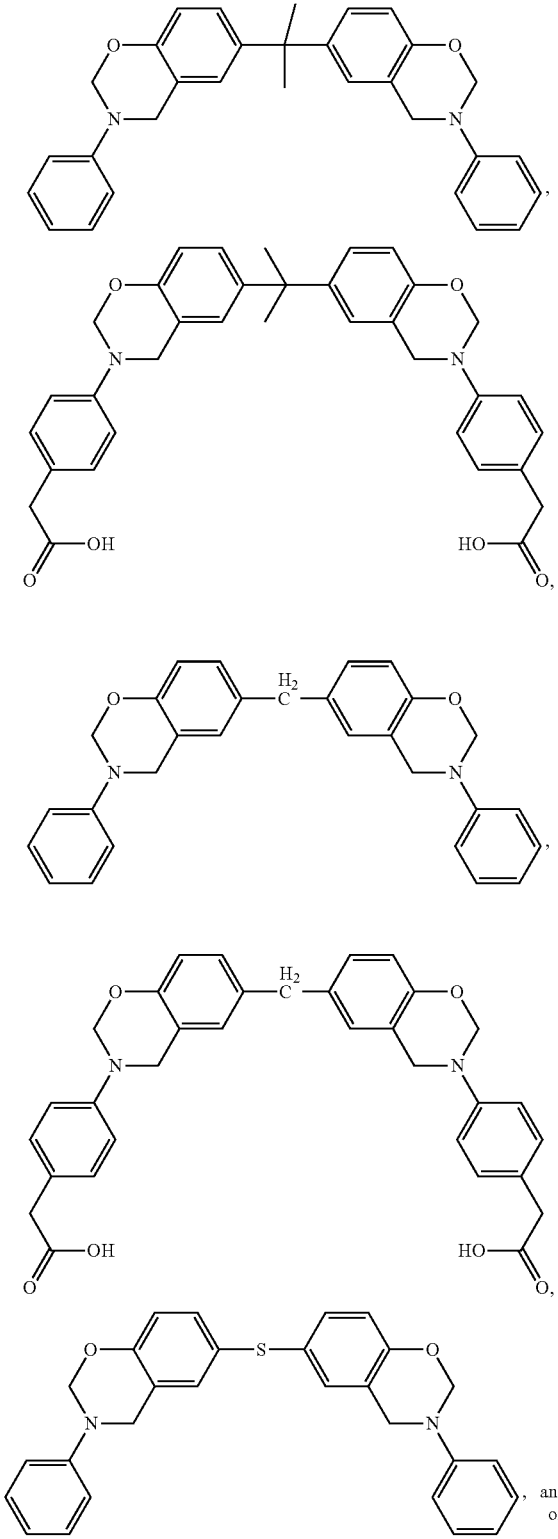

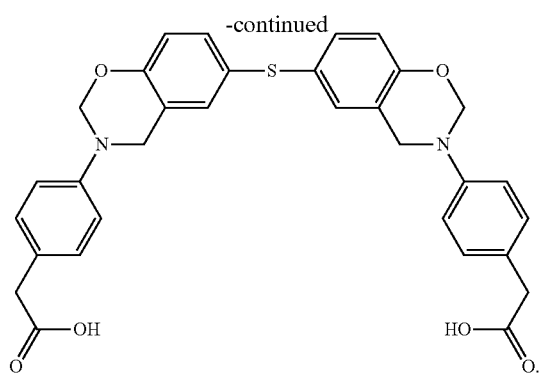

In some embodiments of the present disclosure, at least a portion of the composition may be bioderived.

An aspect of the present disclosure is a composition having a structure that includes at least one of

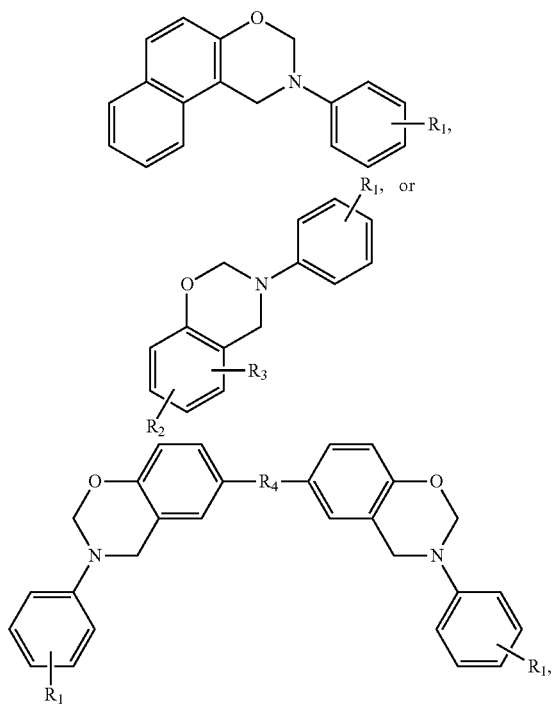

where each of $R_1$, $R_2$, and $R_3$ includes at least one of hydrogen, carbon, and/or fluorine, and $R_4$ includes at least one of carbon, hydrogen, and/or sulfur. In some embodiments of the present disclosure, $R_1$ may include at least one of hydrogen, fluorine, a carboxyl group, a hydroxyl group, an alkoxy group, and/or a hydrocarbon chain. In some embodiments of the present disclosure, $R_2$ may include at least one of hydrogen, fluorine, a carboxyl group, a hydroxyl group, an alkoxy group, and/or a hydrocarbon chain. In some embodiments of the present disclosure, $R_3$ may include at least one of hydrogen, fluorine, a carboxyl group, a hydroxyl group, an alkoxy group, and/or a hydrocarbon chain. In some embodiments of the present disclosure, $R_4$ may include at least one of carbon and/or sulfur.

In some embodiments of the present disclosure, the composition may have a structure that includes at least one of

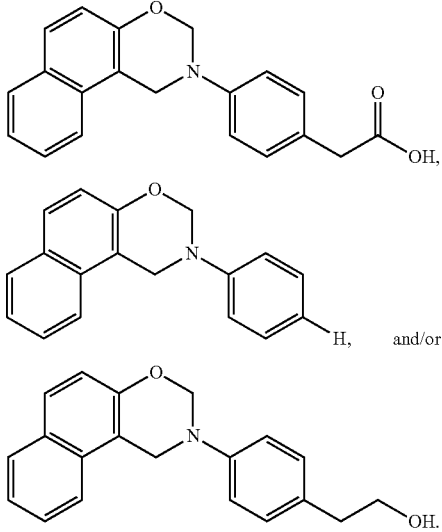

In some embodiments of the present disclosure, the composition may have a structure that includes at least one of

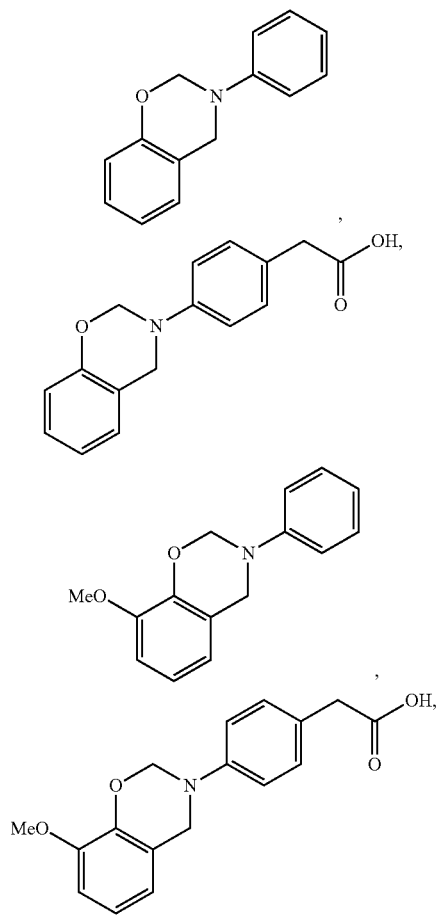

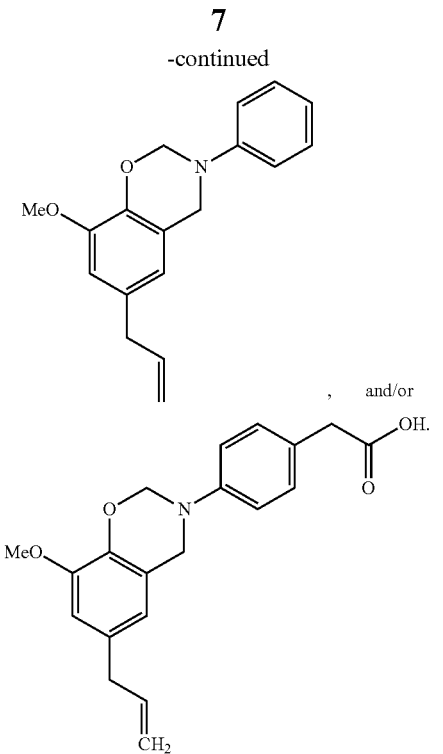

In some embodiments of the present disclosure, the composition may have a structure that includes at least one of

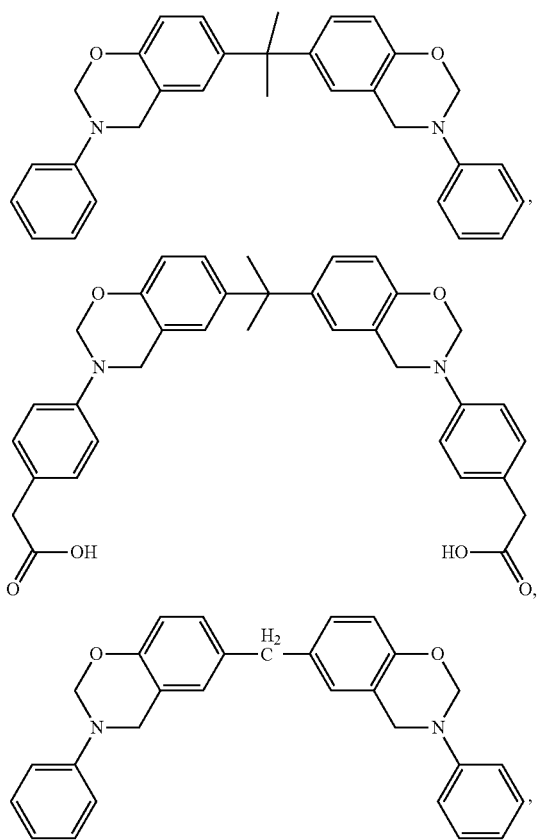

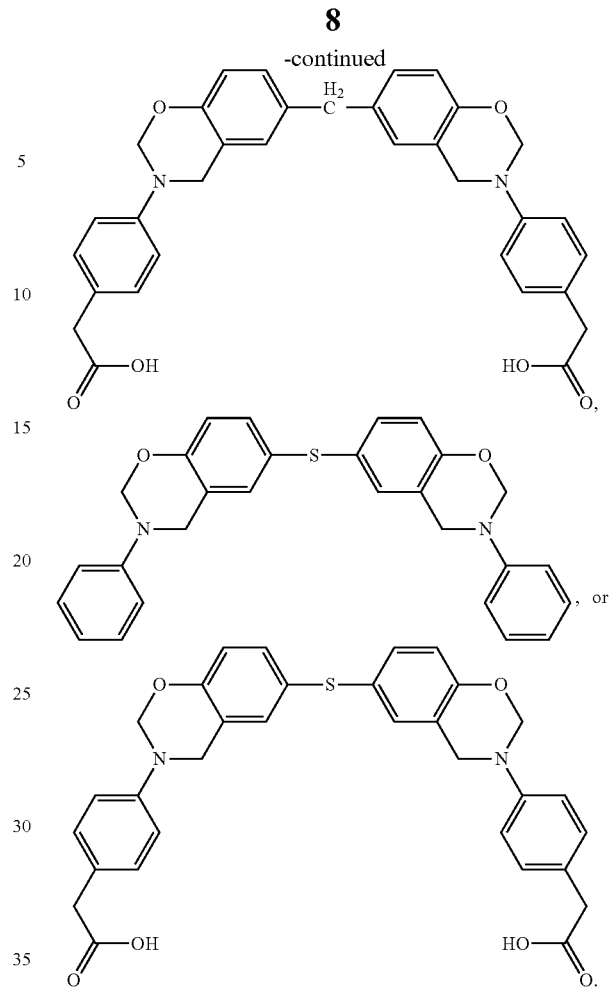

BRIEF DESCRIPTION OF DRAWINGS

Some embodiments are illustrated in referenced figures of the drawings. It is intended that the embodiments and figures disclosed herein are to be considered illustrative rather than limiting.

DETAILED DESCRIPTION

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

Figure 1:
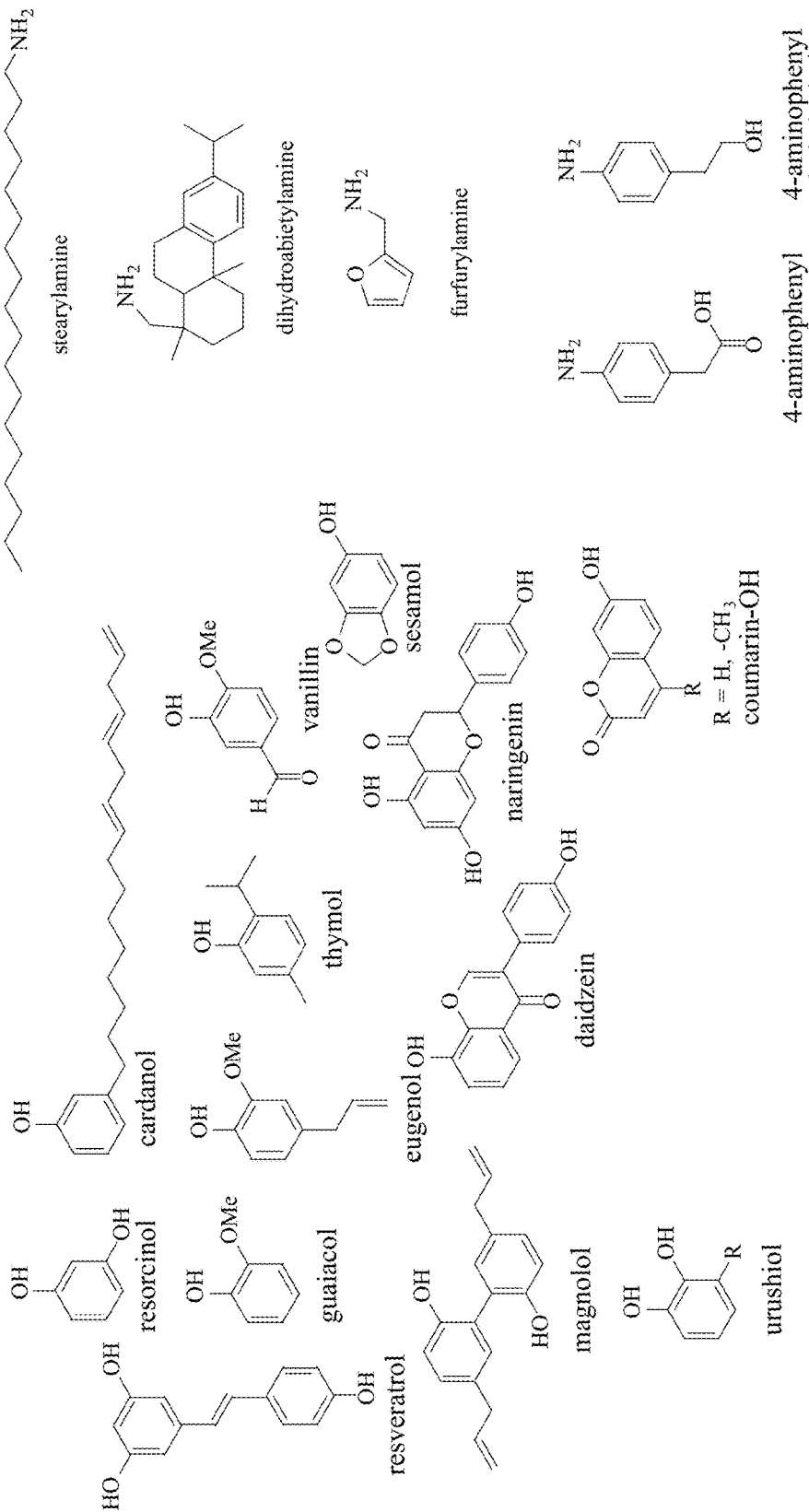
FIG. 1 illustrates various bioderived phenol and amine monomers capable of generating molecules as described herein, according to some embodiments of the present disclosure. Among other things, R may be —$(CH_2)_{14}CH_3$, —$(CH_2)_7CH=CH(CH_2)_5CH_3$, —$(CH_2)_7CH=CHCH_2CH=CH(CH_2)_2CH_3$, —$(CH_2)_7CH=CHCH_2CH=CHCH=CHCH_3$, —$(CH_2)_7CH=CHCH_2CH=CHCH2CH=CH_2$.

Among other things, the present disclosure relates to the conversion of bioderived molecules to benzoxazines monomers, for example, naphthoxazines, which may then be subsequently polymerized to make polybenzoxazines, e.g., polynaphthoxazines, and resins. In general, as described herein, the reaction to make benzoxazine monomers includes reacting a phenolic compound with a primary amine and formaldehyde and/or a paraformaldehyde. FIG. 1 illustrates some examples of biobased phenols and biobased amines. Reaction 1 illustrates an exemplary reaction, the reacting of 2-naphthol with 4-aminophenyl acetic acid and paraformaldehyde to produce a naphthoxazine, according to some embodiments of the present disclosure.

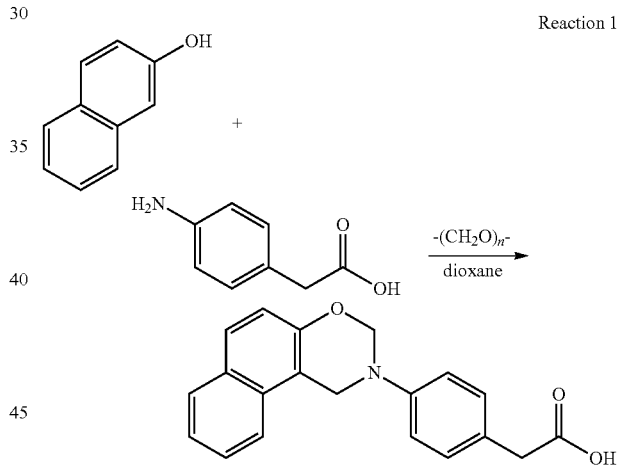

Reaction 1

Reactions 2 and 3 illustrate two other reactions of 2-naphthol and paraformaldehyde with 4-aminophenyl ethyl alcohol and aniline, respectively, to produce two more exemplary naphthoxazines, according to some embodiments of the present disclosure.

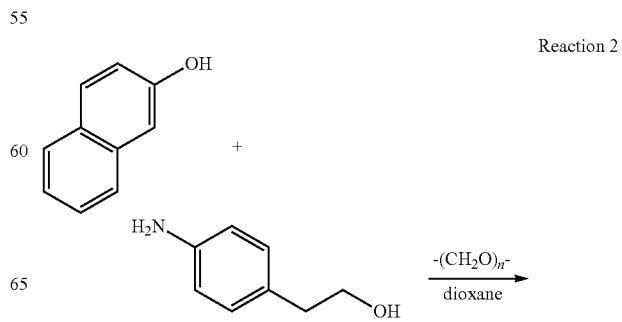

Reaction 2

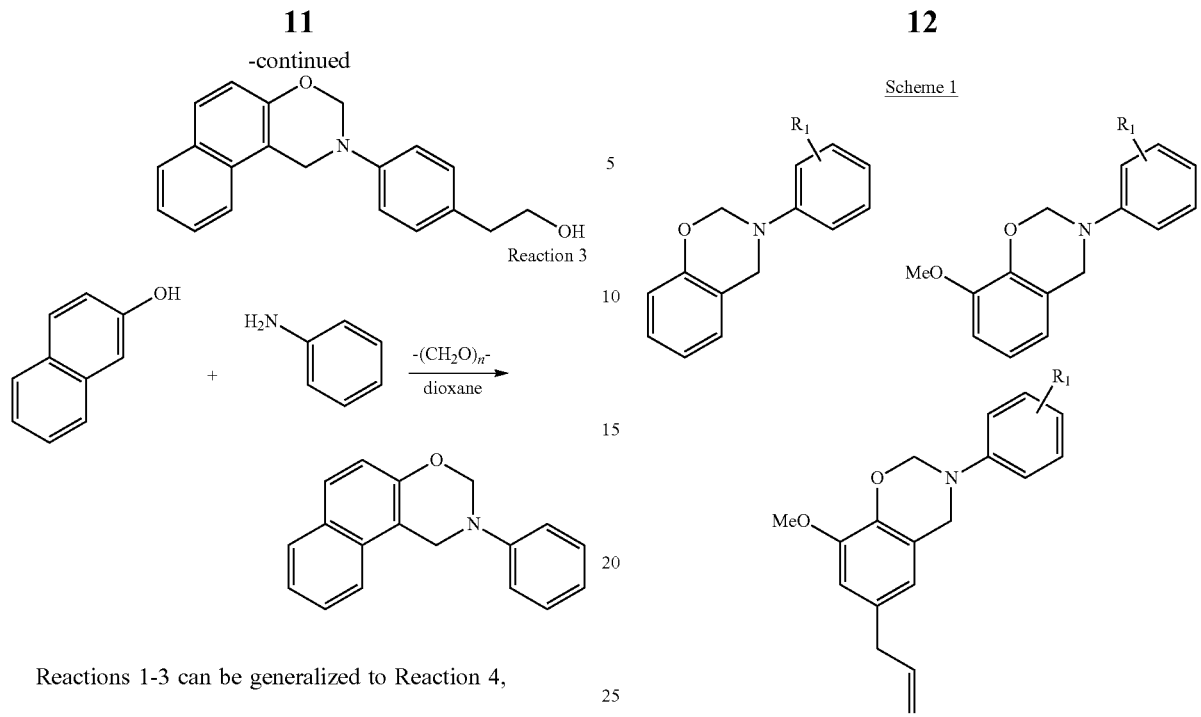

Reactions 1-3 can be generalized to Reaction 4,

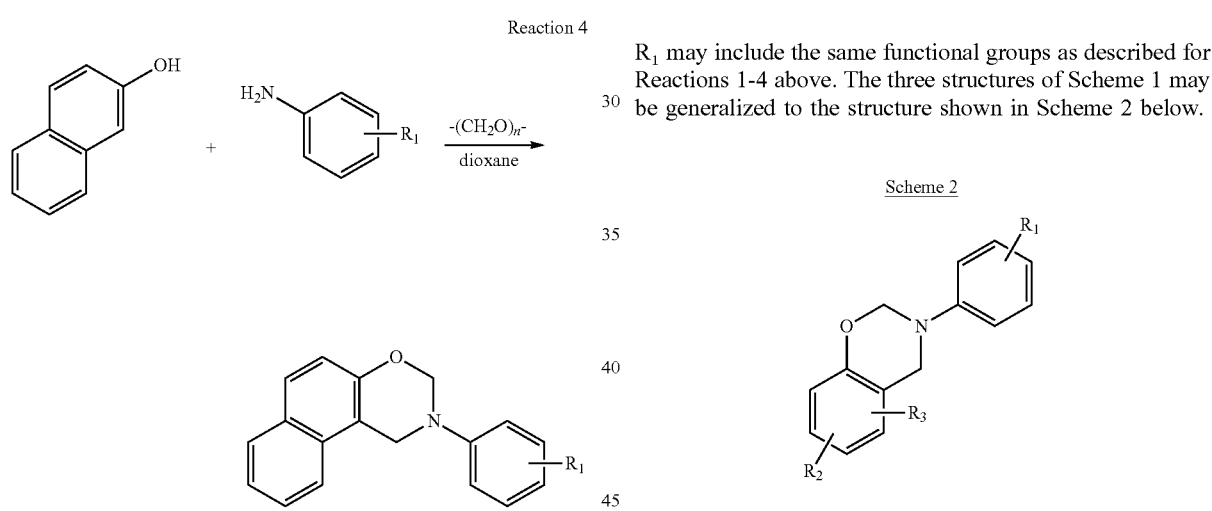

where $R_1$ may include a hydrogen atom, a carbon atom, and/or a hydrocarbon chain. In some embodiments of the present disclosure, $R_1$ may be a hydrocarbon chain functionalized with at least one of a carboxylic acid group, a hydroxyl group, an oxygen atom, an amine, a nitrogen atom, and/or a sulfur atom. $R_1$ may be a straight-chained hydrocarbon or a branched hydrocarbon chain. $R_1$ may be a saturated hydrocarbon chain or an unsaturated hydrocarbon chain.

Reactions 1-4 show some embodiments of the present disclosure for illustrative purposes. However, the same generalized chemistry may also be applied using instead of 2-naphthol, phenol and various functionalized phenolic molecules, such as 2-methoxyphenol, and 2-methoxy-5-(2-propen-1-yl)-phenol. The resultant structures that may be synthesized by reacting with phenol, 2-methoxyphenol, and 2-methoxy-5-(2-propen-1-yl)-phenol, respectively, with the same generalized amine as shown in Reaction 4 are summarized in Scheme 1 below.

$R_1$ may include the same functional groups as described for Reactions 1-4 above. The three structures of Scheme 1 may be generalized to the structure shown in Scheme 2 below.

In Scheme 2, $R_1$ may be as defined above. Similarly, both $R_2$ and $R_3$ may include a hydrogen atom, a carbon atom, and/or a hydrocarbon chain. In some embodiments of the present disclosure, both $R_2$ and $R_3$ may be a hydrocarbon chain functionalized with at least one of a carboxylic acid group, a hydroxyl group, an oxygen atom, an amine, a nitrogen atom, and/or a sulfur atom. both $R_2$ and $R_3$ may be a straight-chained hydrocarbon or a branched hydrocarbon chain. both $R_2$ and $R_3$ may be a saturated hydrocarbon chain or an unsaturated hydrocarbon chain. $R_2$ and $R_3$ may be the same functional group or atom, or they may be different.

Other examples of more complex structures that may be obtained include those resulting from the reacting of 4-aminophenyl acetic acid or aniline with paraformaldehyde and bisphenol molecules such as Bisphenol A, 4,4'-methylenebisphenol (Bisphenol F), and 4,4'-thiodiphenol. The structures resulting from reacting the same generalized amine as shown in Reaction 4 with Bisphenol A, 4,4'-methylenebisphenol (Bisphenol F), and 4,4'-thiodiphenol, respectively, are summarized in Scheme 3 below.

Scheme 3

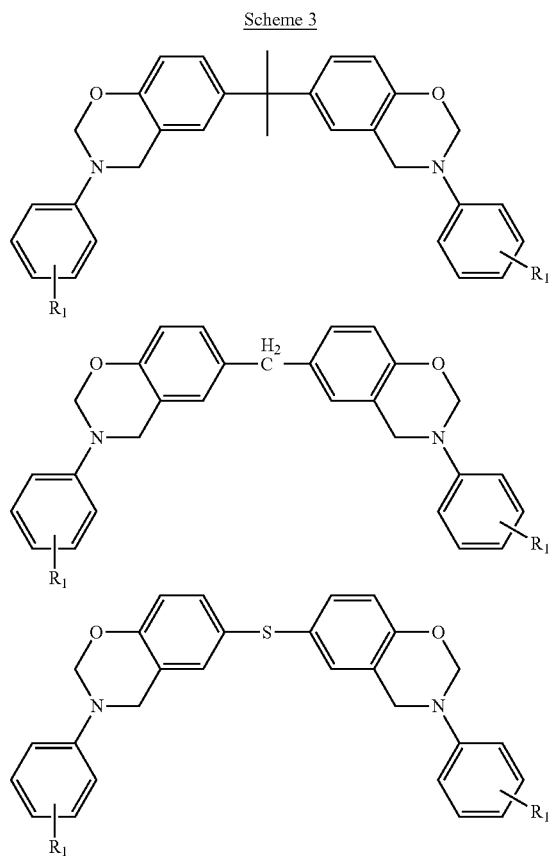

The three structures of Scheme 3 may be further generalized to the structure shown in Scheme 4 below.

Scheme 4

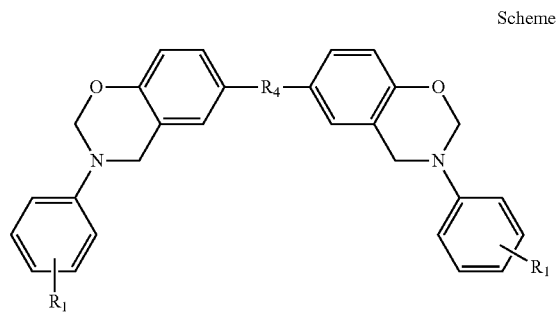

$R_1$ may be as defined above. $R_4$ may include at least one of a carbon atom, hydrogen, fluorine, and/or a sulfur atom.

Reactions 1-4 above illustrate routes to synthesize a variety of molecules as summarized in Schemes 1-4. To enable better conversion and yields to the desired target molecules, in some situations, it may be beneficial to modify the chemistry shown in Reactions 1-4 with the use of a protecting group. For example, referring to Reaction 1 above, the reactivity of the carboxyl group of the 4-aminophenyl acetic acid may result in undesirable side reactions. The use of a protecting group may minimize these reactions. Reaction 5 illustrates a modified version of Reaction 1 that utilizes a protecting group, according to some embodiments of the present disclosure.

Reaction 5

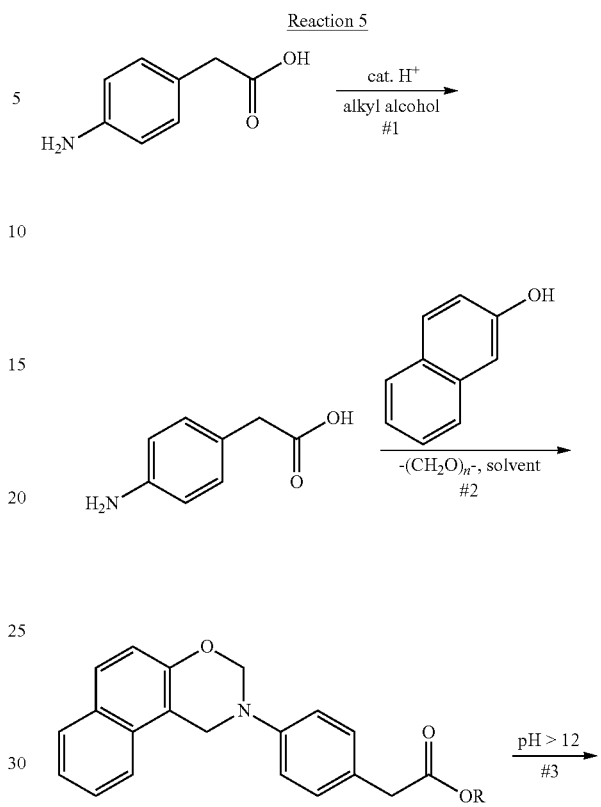

Step #1 of Reaction 5 reacts 4-aminophenyl acetic acid with an alkyl alcohol, ROH, resulting in the "protection" of the carboxylic acid group with the protecting group R. R may be any straight-chained or branched hydrocarbon, saturated or unsaturated with examples of R including a methyl group, an ethyl group, an i-propyl group, a t-butyl group, etc. Once the carboxylic acid group is capped, the equivalent to Reaction 1 is completed, Step #2 in Reaction 5, to produce the protected version of the oxazine-containing molecule, at potentially higher yields. Finally, in Step #3, the protecting group is removed to produce the same final target molecule, as achieved in Reaction 1. The same sort of protecting group approach may be used for any of the oxazine-containing molecules described above and/or shown in Reactions 1-4 and Schemes 1-4.

In some embodiments of the present disclosure, the oxazine-containing molecules described above may be used as monomers to produce novel polymers and/or resins. This may be achieved by an acid-catalyzed ring-opening reaction of the oxazine. This is summarized in Reactions 6 and 7 below for benzoxazine molecules and naphthoxazine molecules, resulting in polybenzoxazines and polynaphthoxazines, respectively (Reaction 7 illustrates reacting the molecule produced in Reaction 4 above).

Reaction 6

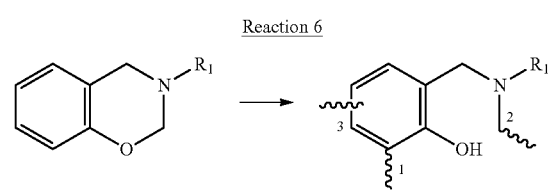

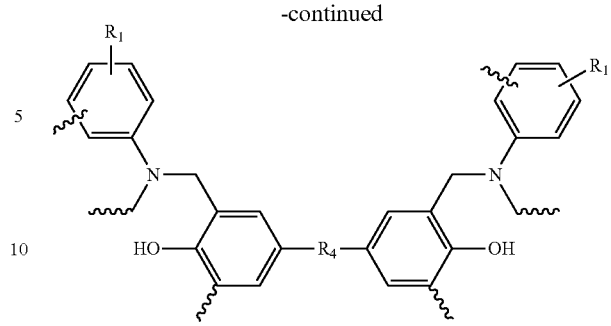

Reaction 7

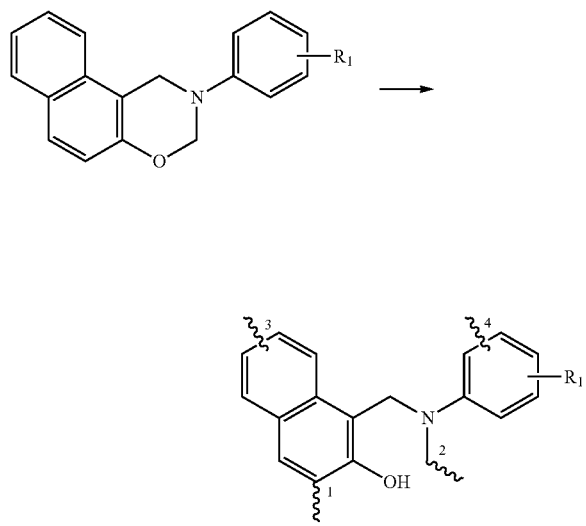

Note that in both reactions that the oxazine ring opens to form two bonds (labeled 1 and 2) with neighboring ring-opening oxazine-containing monomers. In some embodiments of the present disclosure, only bonds 1 and 2 will form, resulting in a polymer. However, as indicated in Reactions 6 and 7, in some embodiments of the present disclosure, additional bonds (labeled 3 and 4) may also form during the reactions originating from the aromatic functional groups; e.g., benzene rings and/or naphthalene rings. Bonds 3 and 4 may form bridges to other ring-opened oxazine functional groups and/or to other aromatic groups. Therefore, the products shown in Reactions 6 and 7 may form polymers and/or resins. Similar polymers/resins may be produced using any of the products shown in Reactions 1-5 and summarized in Schemes 1-4. These are summarized below in Scheme 5 (from Scheme 2 and Scheme 4, respectively).

Scheme 5

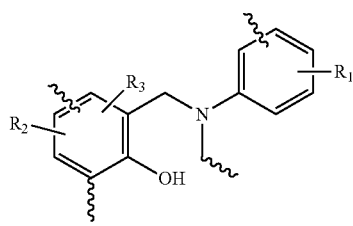

As described above, the present disclosure relates to the synthesis, using the reactions shown above, of naphthoxazines (among other molecules) with biofunctionality from biobased (i.e., bioderived) aromatic amines and/or phenolic molecules. The synthesized structures were studied by $^1$H NMR spectroscopy, $^{13}$C NMR spectroscopy, differential scanning calorimetry (DSC), and Fourier transform infrared (FT-IR) spectroscopy. The resulting polynaphthoxazines were analyzed by thermogravimetric analysis (TGA) as well as FT-IR spectroscopy. The naphthoxazines were analyzed as both a pure material and as an additive with a control naphthoxazine and 1,3-bis(benzoxazine) and demonstrated low polymerization temperatures at low mole percentages.

Figure 2:
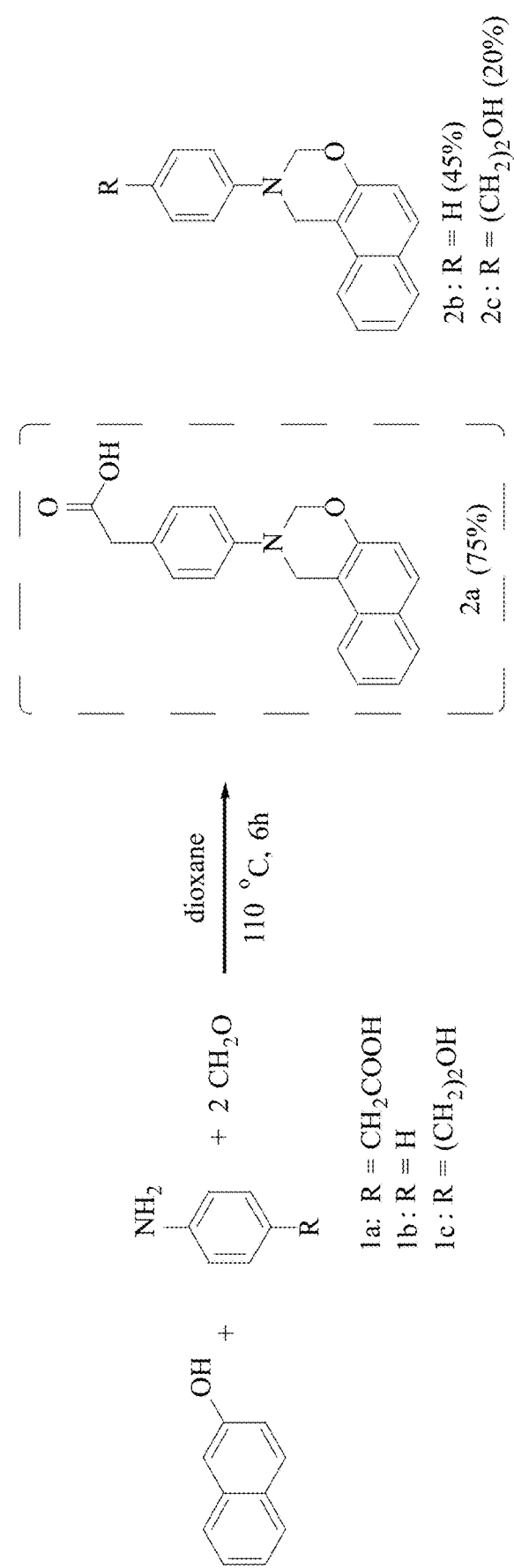
FIG. 2 illustrates a general synthesis scheme for producing naphthoxazines, according to some embodiments of the present disclosure.

FIG. 2 illustrates a schematic for the synthesis of naphthoxazines. The synthesis method for producing the naphthoxazine was designed to accommodate the solubilization of the bio-based amines, both 4-aminophenyl acetic acid (1a) and 4-aminophenylethyl alcohol (1c). 2-naphthol was selected as the phenolic monomer to impart more rigidity and aromatic content in the backbone of the resulting polymer/resin and to increase the sensitivity to thermal degradation of the material compared to phenol. The synthesis was carried out in a one-pot Mannich reaction, with the resulting reactions cooled to room temperature. Molecules 2a and 2c precipitated from solution and recrystallized to yield yellow powders of 75% and 20%, while molecule 2b was further purified through column chromatography. After purification, molecule 2b was a dark orange, viscous oil at 45% yield.

Figure 3:
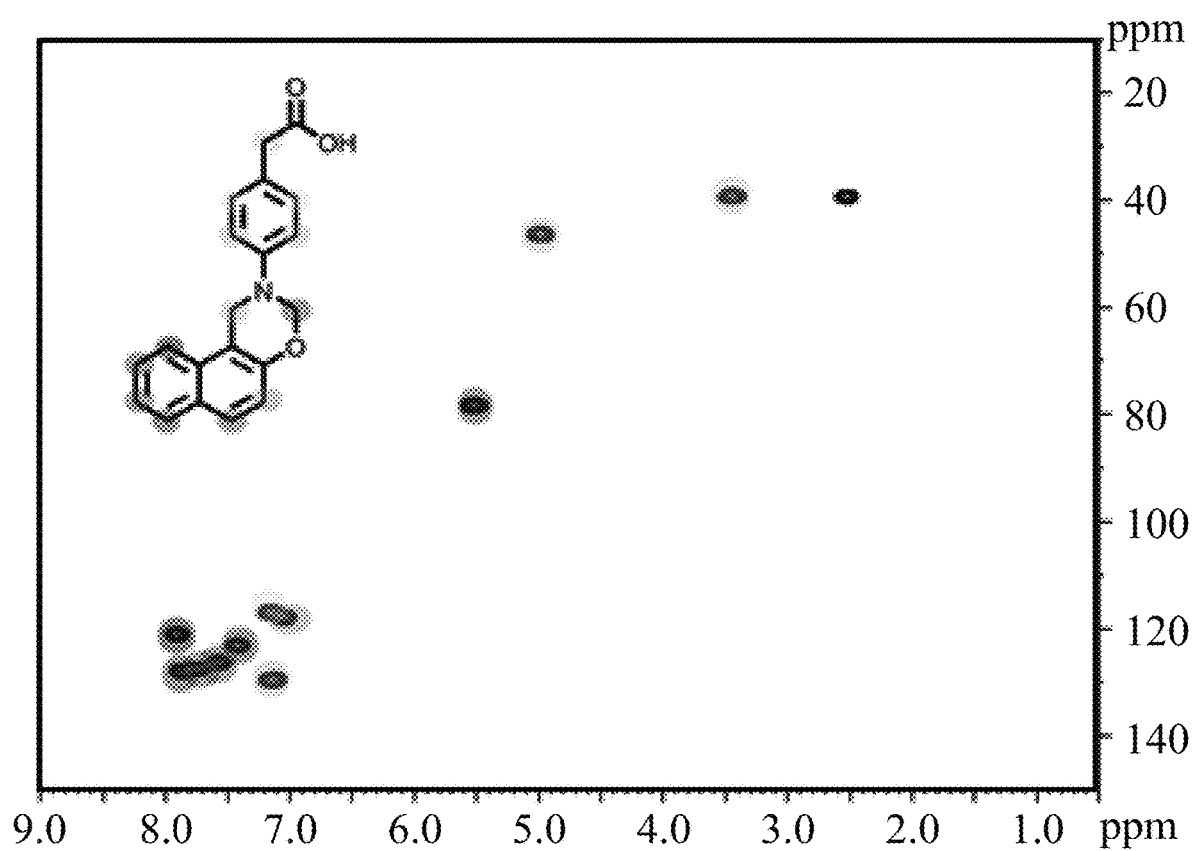
FIG. 3 illustrates heteronuclear single quantum coherence NMR (HSQC) data of molecule 2a (from FIG. 2) in DMSO-$d_6$ at 25° C., according to some embodiments of the present disclosure.

Structural characterization was carried out on the three naphthoxazines illustrated in FIG. 2 using HSQC methods to assign $^1$H and $^{13}$C shifts to verify pure product was formed with no remaining isomers. Referring to FIG. 3 (with details tabulated in Table 1), the identification of clear singlets from the Ar—CH$_2$—N at 4.96 ppm and the N—CH$_2$—O at 5.50 ppm are indicative peaks from the formation of a benzoxazine ring. Further evidence of the benzoxazine formation can be seen in the aromatic splitting pattern below in Table 1. If the formation of the benzoxazine ring were to occur in the 2 and 3 positions of the naphthol ring, there would be two singlets in the aromatic region corresponding to the neighboring quaternary carbons on either side of the aromatic protons. However, in this case, two doublets are observed at 7.02 ppm (neon green) and 7.71 ppm (grey) with corresponding $^{13}$C signals at 119.3 ppm and 128.1 ppm. HSQC spectra of both molecules 2b and 2c display signature benzoxazine peaks at similar shifts.

TABLE 1

$^1$H, $^{13}$C, and HSQC Data

| Naph-aniline (2b) | | Naph-COOH (2a) | | Naph-OH (2c) | |
|---|---|---|---|---|---|
| $^1$H, $^{13}$C (ppm) | Corresponding H's | $^1$H, $^{13}$C (ppm) | Corresponding H's | $^1$H, $^{13}$C (ppm) | Corresponding H's |
| 4.98, 47.8 | s, 2H Ar—CH$_2$—N | 3.43, 39.4 | s, 2H, —CH$_2$—COOH | 2.60, 39.2 | t, 2H, Ar—CH$_2$—CH$_2$ |
| 5.52, 79.6 | s, 2H N—CH$_2$—O | 4.96, 47.8 | s, 2H, Ar—CH$_2$—N | 3.05, 63.3 | q, 2H, —CH$_2$—CH$_2$—OH |
| 6.86, 121.5 | t, 1H | 5.50, 79.8 | s, 2H, N—CH$_2$—O | 4.51 | t, —OH |
| 7.02, 119.4 | d, 1H | 7.02, 119.3 | d, 1H | 4.95, 48.0 | s, 2H Ar—CH$_2$—N |
| 7.18-7.26, 118.4, 130.1 | m, 4H | 7.10-7.15, 118.4, 130.9 | m, 4H | 5.49, 79.9 | s, 2H, N—CH$_2$—O |
| 7.38-7.42, 124.6 | m, 1H | 7.38-7.42, 124.6 | m, 1H | 7.01, 119.4 | d, 1H |
| 7.52-7.57, 127.7 | m, 1H | 7.53-7.57, 127.7 | m, 1H | 7.06-7.11, 118.5, 131.9 | m, 4H |
| 7.72, 129.0 | d, 1H | 7.71, 128.1 | d, 1H | 7.37-7.41, 124.5 | m, 1H |
| 7.84, 129.4 | d, 1H | 7.84, 128.9 | d, 1H | 7.52-7.56, 127.7 | m, 1H |
| 7.89, 122.5 | d or dd, 1H | 7.88, 122.5 | d, 1H | 7.71, 128.9 | d, 1H |
| C4s: 152.7, 149.0, 132.0, 129.4, 113.9 | | 12.17, 173.8 | bs, 1H —COOH | 7.83, 130.5 | d, 1H |
| | | C4s: 152.7, 147.7, 132.0, 129.4, 113.9 | | 7.87, 122.4 | d, 1H |
| | | | | C4s: 152.7, 147.2, 132.7, 129.4, 113.9 | |

Figure 4:
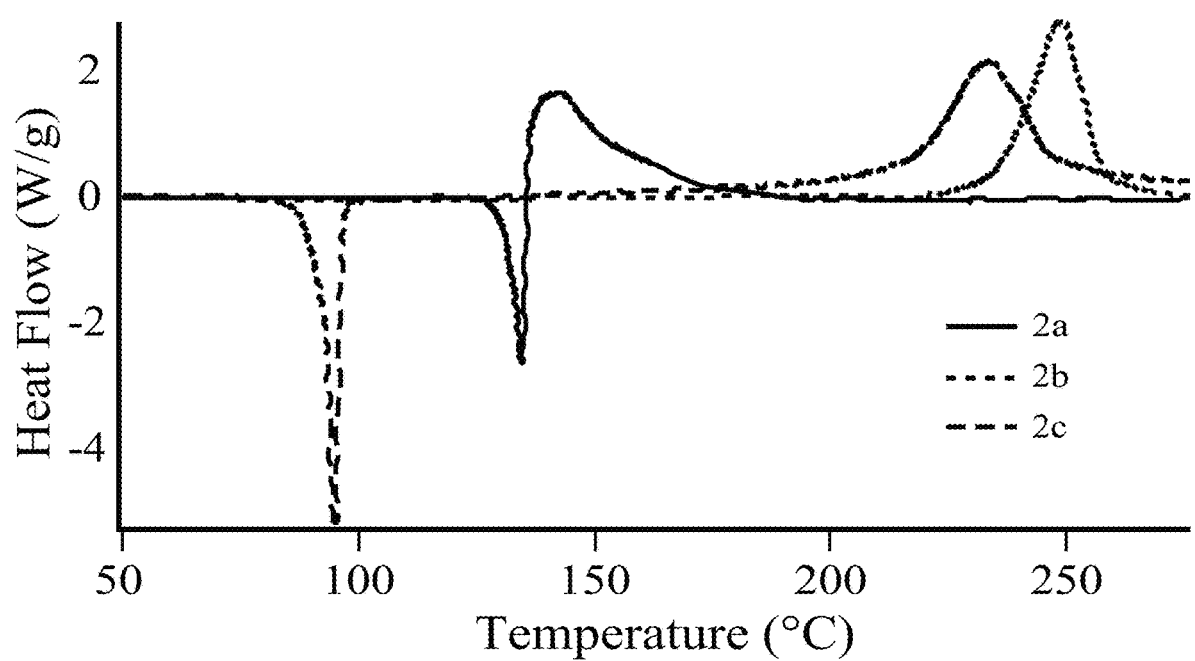
FIG. 4 illustrates differential scanning calorimetry (DSC) thermograms of molecule 2b compared to molecule 2c and molecule 2a (from FIG. 2) at a heating rate of 5° C./min, according to some embodiments of the present disclosure.

The curing behavior of the three naphthoxazines summarized in FIG. 2 was investigated by DSC. FIG. 4 displays the exotherms of molecules 2a, 2b, and 2c. The control molecule 2b displays an exotherm around 249° C., which corresponds to curing occurring. The addition of catalytic moieties covalently incorporated into the bio-based aromatic amine was explored by the thermal characterization of both a naphthoxazine with a primary alcohol and a carboxylic acid. Molecule 2c formed a solid light-yellow powder with a melting point demonstrated by the sharp endothermic peak at 95° C. and the ring-opening of the benzoxazine at 234° C. Molecule 2a also formed a light-yellow solid which displays a sharp melting endotherm at 134° C. but was quickly polymerized with an exotherm peak at 142° C. The decrease in ring-opening temperature may be correlated to the carboxylic acid end group on the bifunctional bio-based amine, which may catalyze the ring opening reaction by increasing the concentration of oxonium species. Though molecule 2c does display a slight decrease in the polymerization exotherm temperature, the carboxylic acid moiety demonstrates higher catalytic activity for lowering the ring-opening polymerization of the naphthoxazine. Thus, molecule 2a was chosen for further investigation into catalytic ring opening of naphthoxazine to evaluate the energetics of this reaction.

Figure 5:
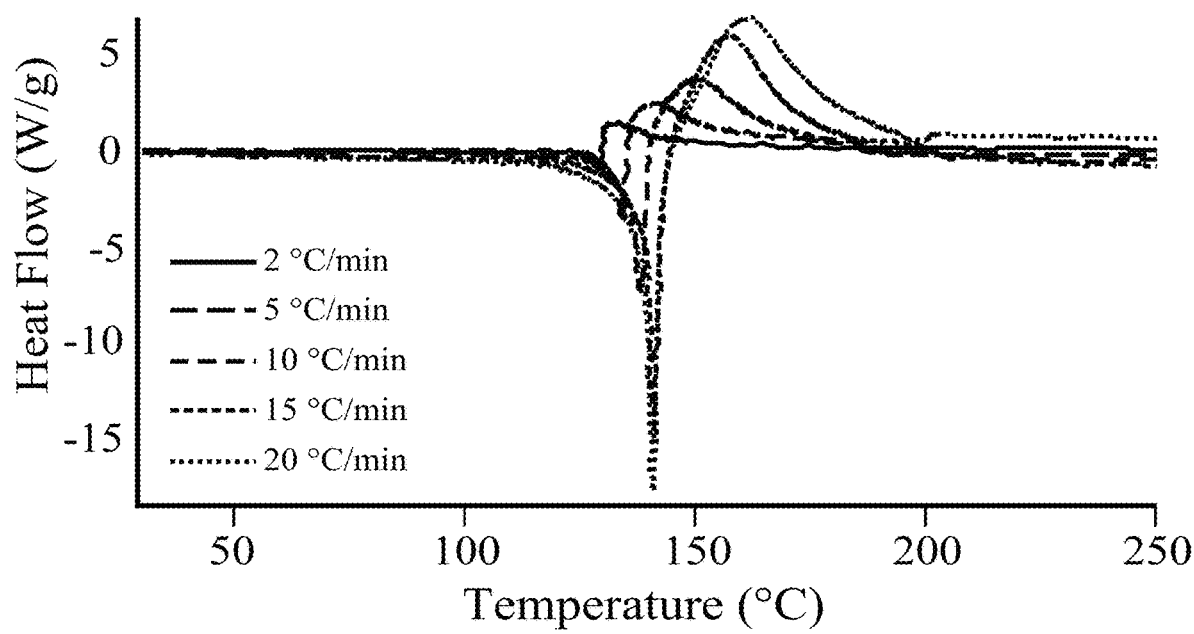
FIG. 5 illustrates DSC thermograms of molecule 2a (from FIG. 2) at heating rates of 2, 5, 10, 15, 20° C./min, according to some embodiments of the present disclosure.
Figure 6:
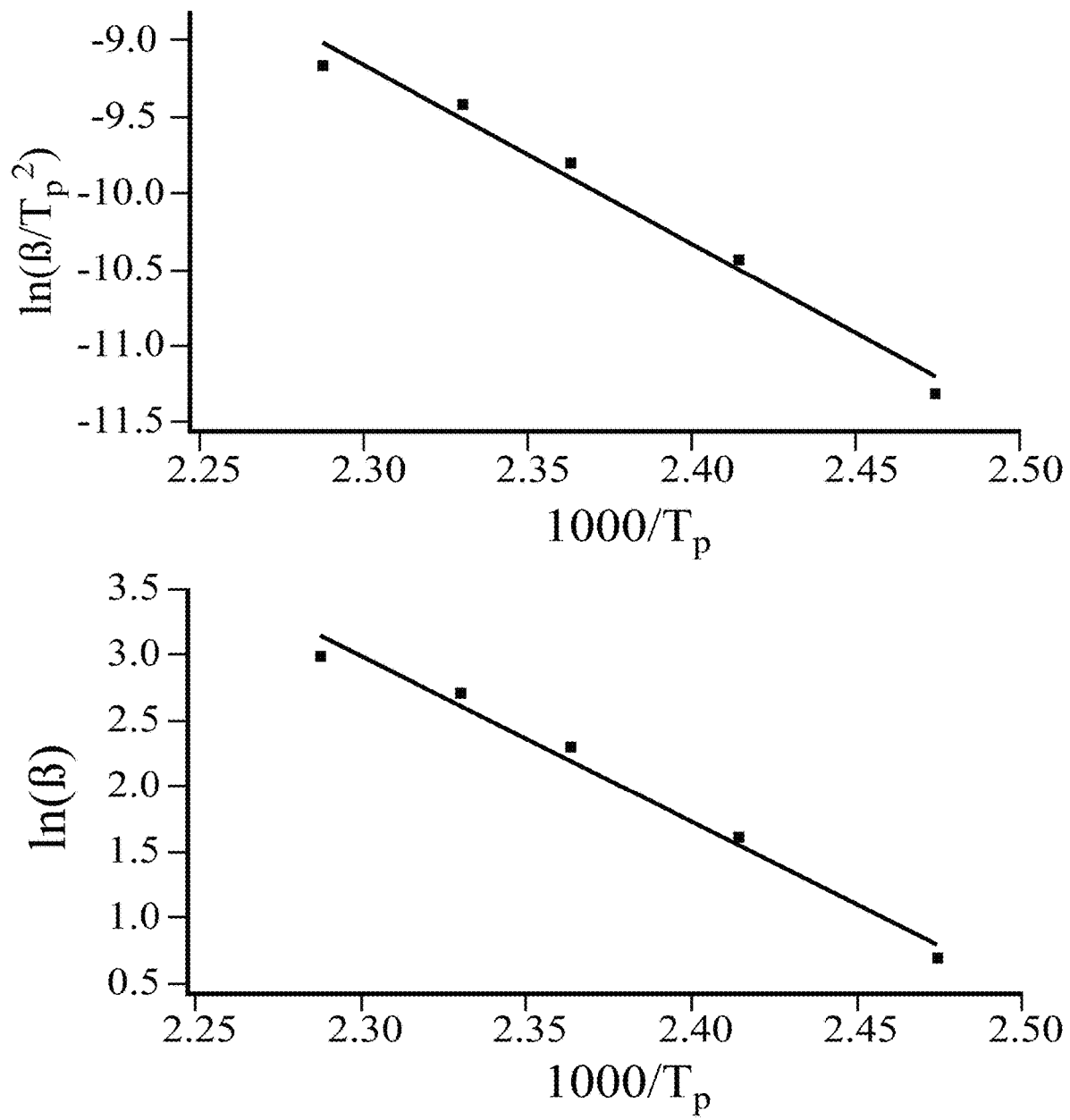
FIG. 6 illustrates plots of Kissinger (top) and Ozawa (bottom) methods for calculating the activation energy of polymerization ($E_a$) of molecule 2a (from FIG. 2), according to some embodiments of the present disclosure.

The polymerization kinetics were studied through non-isothermal DSC heating a 2, 5, 10, 15, and 20° C./min heating ramps as illustrated in FIG. 5. The polymerization temperature exotherm peak, $T_p$, increases with increasing heat rates as to be expected. The activation energy of the polymerization was calculated through two established methods: the Kissinger and Ozawa methods. The Kissinger method is based on Equation 1 as follows:

$$\ln\left(\frac{\beta}{T_p^2}\right) = \ln\frac{AR}{E_a} - \frac{E_a}{RT_p} \quad \text{Equation 1}$$

where $\beta$ is the heating ramp, $T_p$ is the polymerization temperature designated from the peak of the polymerization exotherm, A is the frequency factor, R is the gas constant and $E_a$ is the activation energy. The Ozawa method activation energy is calculated by Equation 2:

$$\ln(\beta) = C - 1.052\frac{E_a}{RT_p} \quad \text{Equation 2}$$

with C being a constant. By plotting the data obtained with ln $$\left(\frac{\beta}{T_p^2}\right)$$

or ln($\beta$) on the y-axis as a function of $1/T_p$, the activation energy can be calculated from the slope of the linear plotted data as shown in FIG. 6 (top Kissinger; bottom Ozawa). According to the data collected by both Kissinger and Ozawa methods, the activation energy for polymerization of molecule 2a is calculated to be about 97.8 kJ/mol by the Kissenger method and about 99.5 kJ/mol by the Ozawa method. This result indicates that molecule 2a is readily activated to polymerize.

Figure 7:
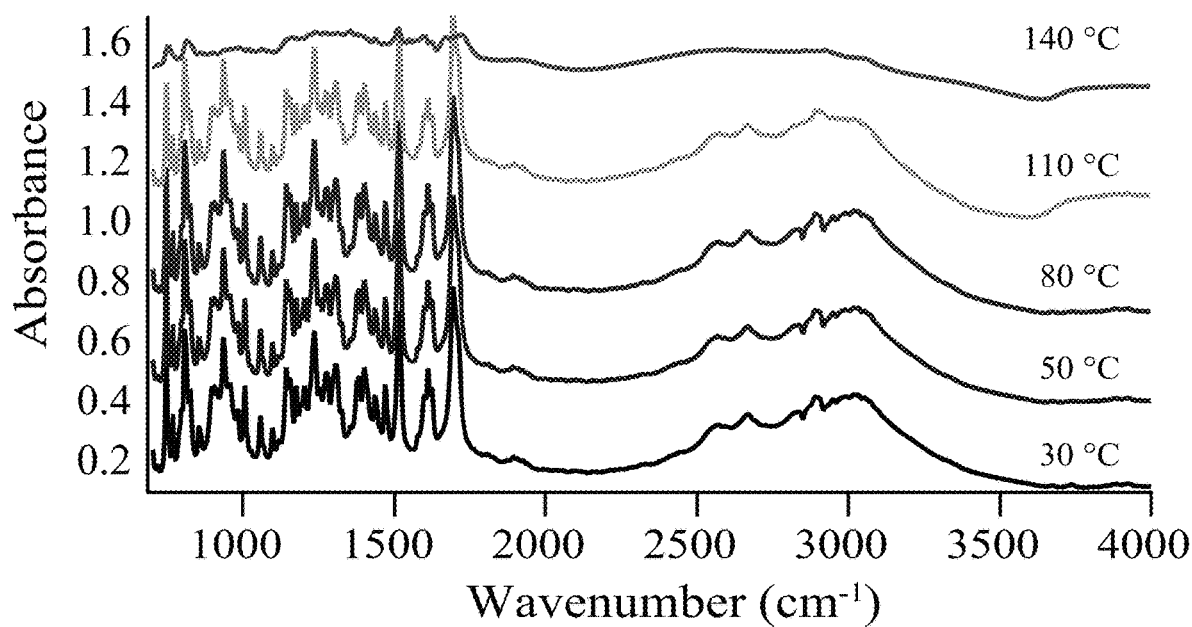
FIG. 7 illustrates FTIR curing data, according to some embodiments of the present disclosure.
Figure 8:
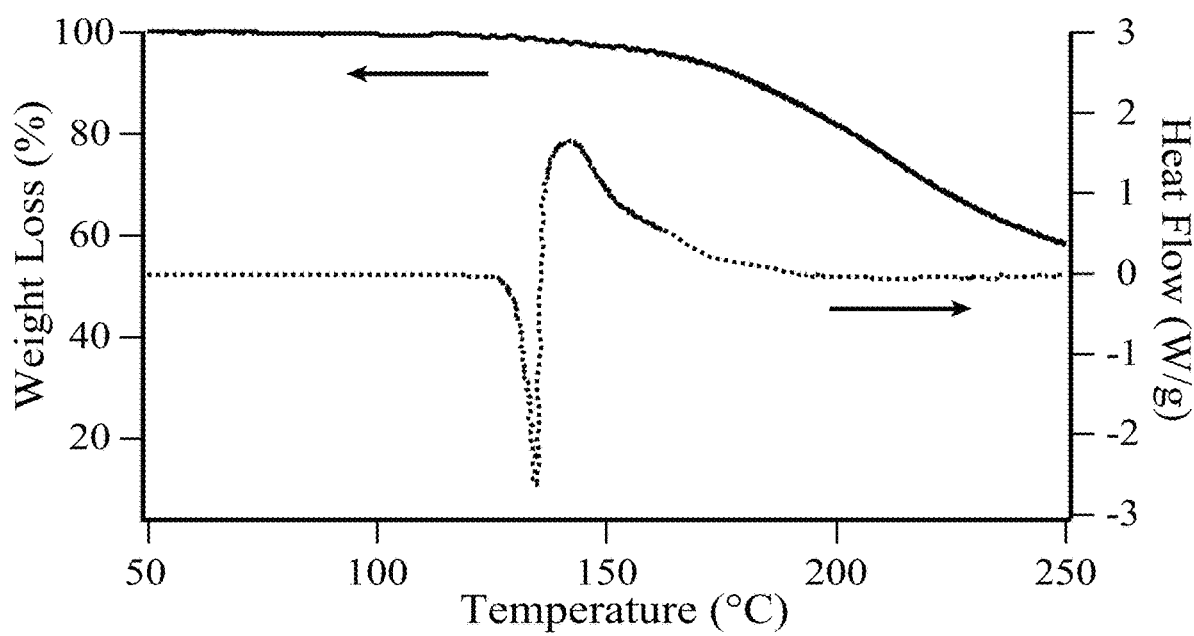
FIG. 8 illustrates thermal characterization of molecule 2a (from FIG. 2) obtained with a 5° C./min ramp rate to demonstrate the beginning of ring opening polymerizations (ROP), according to some embodiments of the present disclosure.

Further investigation into the polymerization behavior of molecule 2a was investigated through FTIR spectroscopy (see FIG. 7). To carry out this analysis, the naphthoxazine monomer was heated to each temperature individually for 30 minutes and analyzed by FTIR. The reduction in absorbance of both the 934 and 1236 cm$^{-1}$ stretches associated with the oxazine ring are indicative of the ring opening of the monomer above 110° C. The oxazine ring opening occurs rapidly once the monomer is melted as expected, at temperatures below the melting temperature of 134° C., the oxazine stretches remain largely unchanged. At temperatures above the melting point of 134° C., the C=O stretch at approximately 1693 cm$^{-1}$ significantly decreased, suggesting the final polymer was partially decarboxylated and the reactivity of the naphthoxazine as an additive was rapid once the monomer was melted as shown in FIG. 8. The overlay of the DSC exotherm with the TGA analysis demonstrates that the ring opening temperature is roughly 35° C. lower than the $T_{d5\%}$ at 167° C., leading to the polymerization of the material prior to degradation with initial weight loss likely due to decarboxylation.

Figure 9:
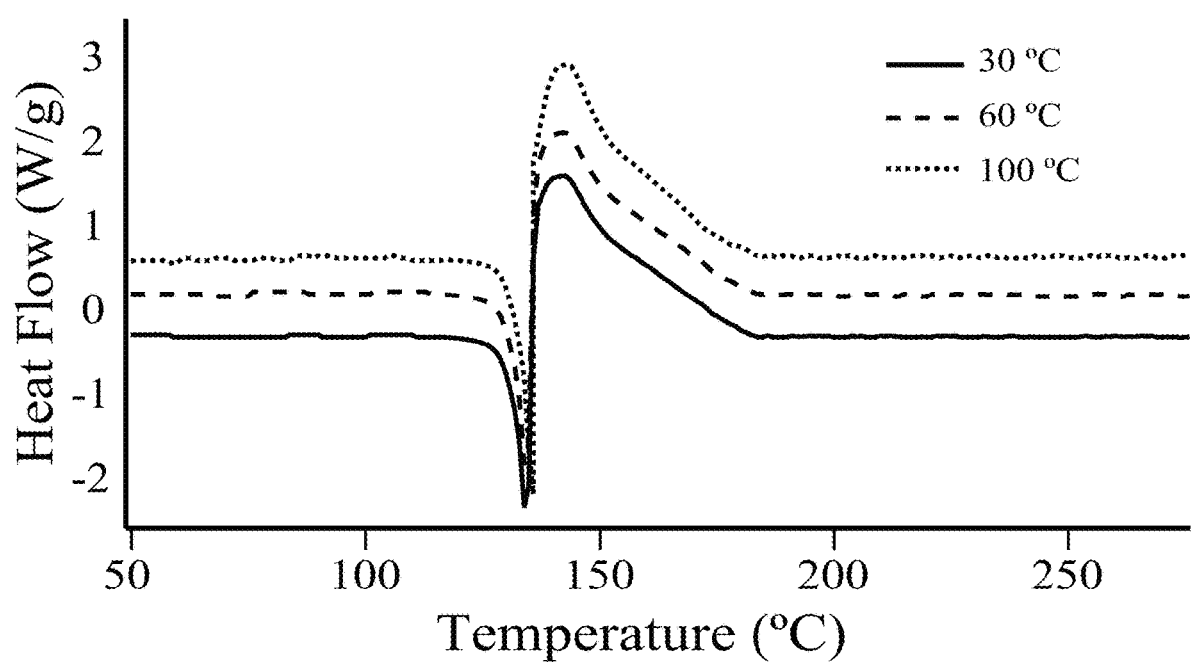
FIG. 9 illustrates DSC thermograms of molecule 2a (from FIG. 2) pretreated at 30° C., 60° C., and 100° C. for one hour with a heating ramp of 5° C./min, according to some embodiments of the present disclosure.
Figure 10:
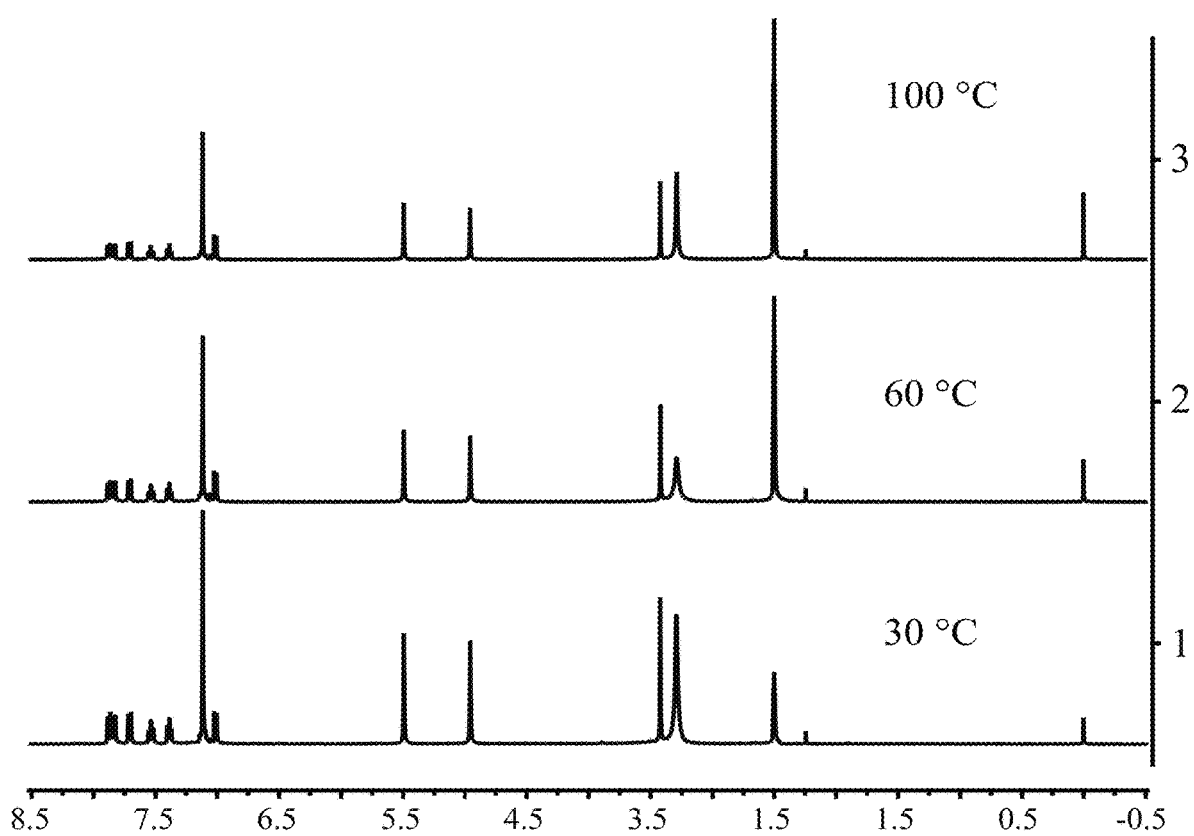
FIG. 10 illustrates $^1$H NMR spectra of molecule 2a (from FIG. 2) at 30, 60, and 100° C. in DMSO-$d_6$, according to some embodiments of the present disclosure.

The stability of the built-in catalytic moiety of molecule 2a was evaluated by analyzing both structural and thermal behavior at various temperatures through heating the compound to various temperatures under the polymerization temperature and examining the polymerization behavior by DSC (see FIG. 9) as well as structural changes through $^1$H NMR (see FIG. 10). The DSC thermograms demonstrate similar polymerization behavior, which indicates the catalytic moiety is stable on these molecules at elevated temperatures and unreacted until melting has occurred. Further, the $^1$H NMR of the pretreated molecule 2a samples exhibits no structural changes as well over the course of two months at ambient temperature. The lack of structural changes under heated and ambient conditions indicates the robust shelf stability of this naphthoxazine will not be prone to degradation over time with an acidic moiety covalently bound to the structure.

Figure 11:
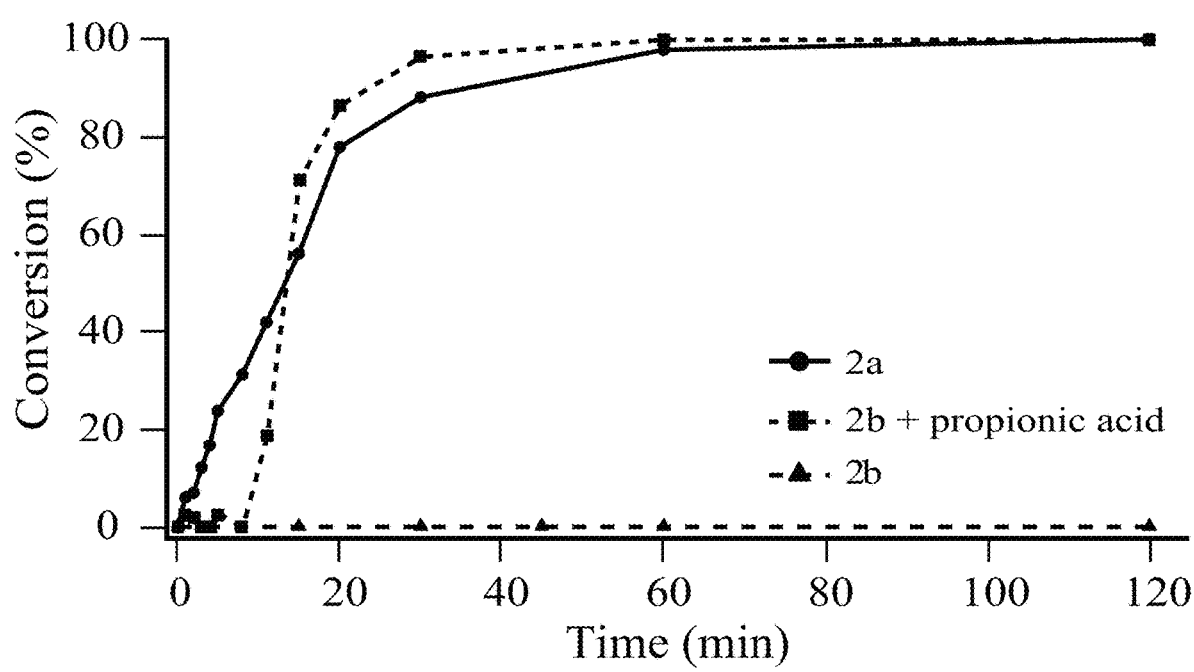
FIG. 11 illustrates the conversion of oxazine ring opening at a temperature of about 130° C. over a time period of about two hours (conversion % vs time (min) by $^1$H NMR, according to some embodiments of the present disclosure, according to some embodiments of the present disclosure.

FIG. 11 demonstrates the monomer conversion of the benzoxazine ring opening with insight into the mechanistic behavior of the carboxylic acid at 130° C. The polymerization kinetics of molecule 2a compared with molecule 2b and addition of the small molecule acid reach similar overall conversions of the ring-opened oxazine with an induction period of approximately 10 minutes using propionic acid as the additional catalyst. The lack of miscibility between these two compounds could explain the induction period. The addition of a small molecule catalyst or initiator greatly reduces the shelf life of the resin thus it is advantageous to build-in catalytic moieties covalently to the molecule which remains stable as a solid. As displayed in FIG. 10, the catalytic moiety does not reduce and impact the shelf life or stability of the bulk material over time or a temperature range of room temperature (30° C.) up to 100° C.

Figure 12:
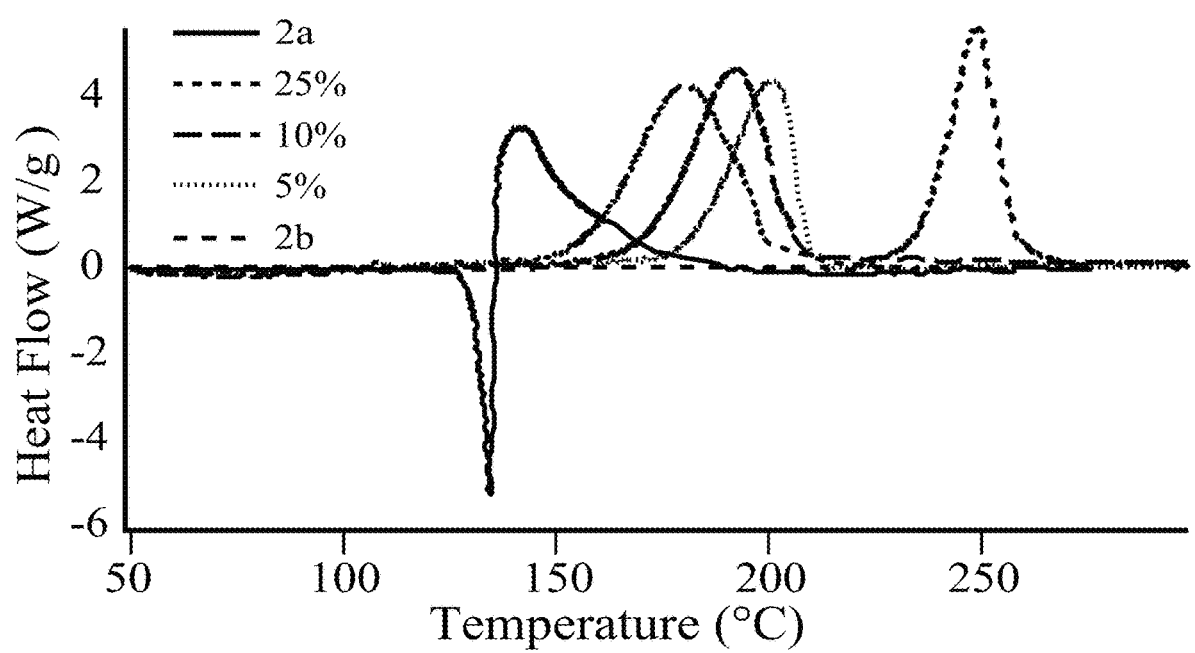
FIG. 12 illustrates DSC thermograms of 5, 10, 25 mol % molecule 2a (from FIG. 2) added to molecule 2b heated at a rate of about C/min, according to some embodiments of the present disclosure.

Next, the affect of reducing polymerization temperatures was evaluated by using molecule 2a as an additive with the control molecule 2b. As can be seen in FIG. 12, the addition of 5, 10, and 25 mol % molecule 2a was added to molecule 2b and the thermograms display a clear decrease in copolymerization temperatures with increasing molecule 2a mol %. The addition of only 5 mol % molecule 2a, displayed a decrease in copolymerization temperature of roughly 50° C., $T_p$=201° C. from 249° C. Further depression of the copolymerization temperatures was observed at 10 mol % molecule 2a $T_p$=192° C. and 25 mol % molecule 2a $T_p$=181° C., though the effect of added carboxylic acid is less dramatic than the initial addition of catalytic molecule 2a. The copolymerization of the molecule 2b with molar additional of molecule 2a displays a thermogram characteristic of molecule 2b rather than displaying a melt temperature of any sort associated with the molecule 2a. Further the addition of 5 mol % of molecule 2a was added and monitored with 1,3-bis(benzoxazine) also referred to FIG. 13, structure 6b. The polymerization of pure 6b is $T_p$=245° C. and with the addition of 5 mol5 2a, there is a copolymerization temperature of 206° C. The addition of molecule 2a at 5 mol % decreased the $T_p$ of the bis(benzoxazine) by about 40° C., thus demonstrating the use of 2a as an effective additive for reducing polymerization temperatures of oxazine-containing materials.

Figure 13:
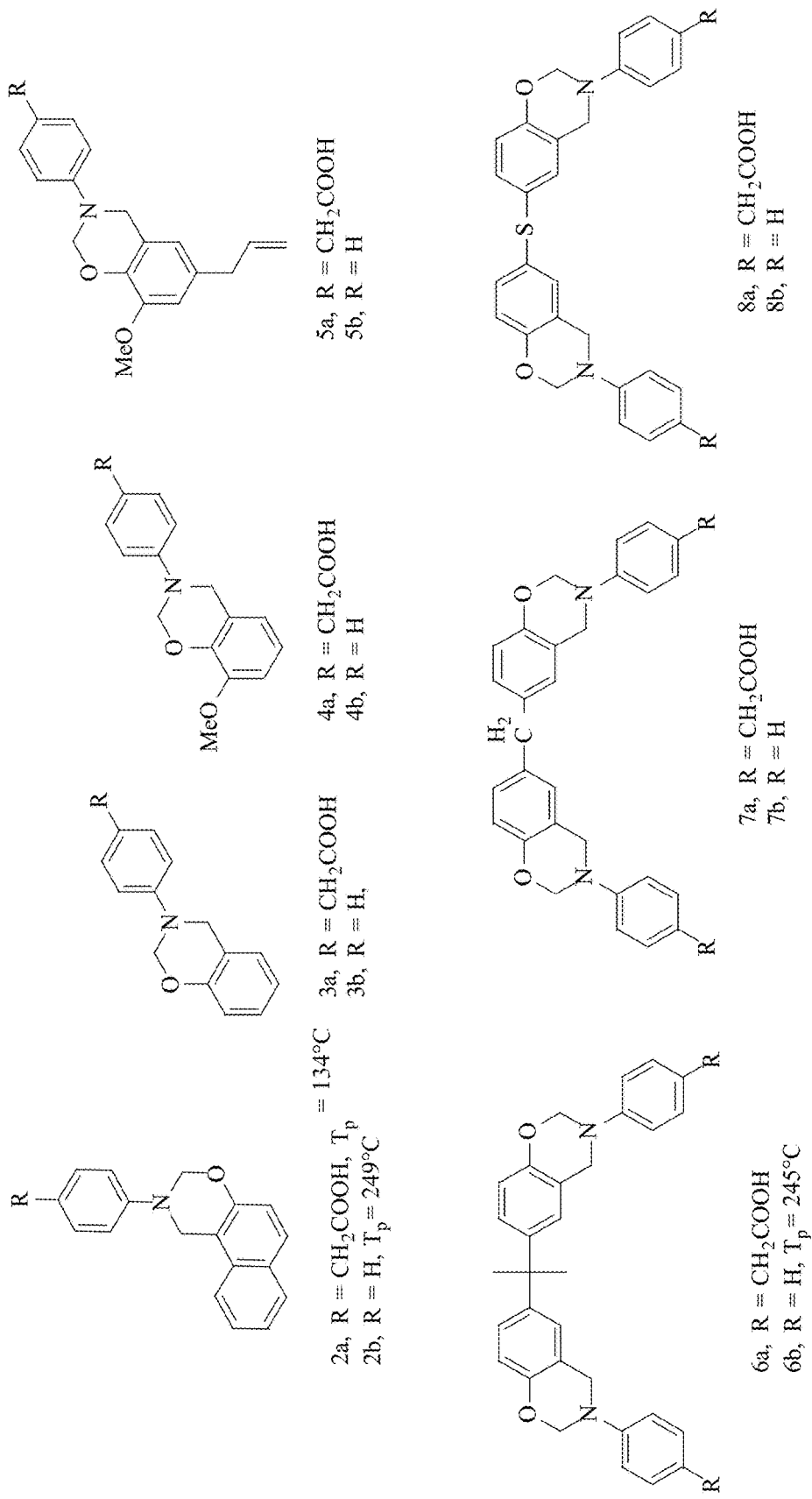
FIG. 13 illustrates other oxazine-containing molecules that may be synthesized and subsequently reacted to form polymer and/or resins, according to some embodiments of the present disclosure.

FIG. 13 illustrates other oxazine-containing molecules that may be synthesized and subsequently reacted to form polymer and/or resins, as described herein, according to some embodiments of the present disclosure.

Experiment Methods

Materials. 2-naphthol (99%), paraformaldehyde (95%), 4-aminophenylacetic acid (98%), 4-aminophenylethyl alcohol (98%), aniline (≥99.5%), and anhydrous 1,4-dioxane (99.8%) was purchased from Sigma Aldrich and used as received. Deuterated DMSO-d$_6$ was purchased from Cambridge Isotopes.

Synthesis of molecule 2a shown in FIG. 2. 2-naphthol (1 mmol), 4-aminophenylacetic acid (1a, 1 mmol), and paraformaldehyde (2 mmol) were refluxed in anhydrous 1,4-dioxane (50 mL) at 110° C. for 6 h. The solution was added dropwise to DI water where the naphthoxazine was precipitated out of the solvent. The obtained yellow powder was crystallized again from dioxane to yield 75% yellow solid. $^1$H NMR (400 MHz, DMSO-d$_6$, ppm): δ=3.43 (s, 2H, —CH$_2$—COOH), 4.96 (s, 2H, Ar—CH$_2$—N), 5.50 (s, 2H, N—CH$_2$—O), 7.02 (d, 1H), 7.10-7.15 (m, 4H), 7.38-7.42 (m, 1H), 7.53-7.57 (m, 1H), 7.71 (d, 1H), 7.84 (d, 1H), 7.88 (d, 1H), 12.17 (bs, 1H—COOH). $^{13}$C NMR (400 MHz, DMSO-d$_6$, ppm): δ=39.4, 47.8, 79.8, 113.9, 118.4, 119.3, 122.5, 124.6, 127.7, 128.1, 128.9, 129.4, 130.9, 132.0, 147.7, 152.7, 173.8. FT-IR (KBr): ν=1236 cm$^{-1}$ (C—O—C asymmetric stretching), 934 cm$^{-1}$ (oxazine-ring mode).

Synthesis of molecule 2c shown in FIG. 2. Similar procedure of 2a followed for production of 2c. 2-naphthol (1 mmol), 4-aminophenylethyl alcohol (1c, 1 mmol), and paraformaldehyde (2 mmol) were refluxed in anhydrous 1,4-dioxane (50 mL) at 110° C. for 6 h. The solution was precipitated into DI water to produce a yellow solid. The yellow solid was crystallized again from dioxane to yield 45%. $^1$H NMR (400 MHz, DMSO-d$_6$, ppm): δ=2.60 (t, 2H, Ar—CH$_2$—CH$_2$), 3.05 (q, 2H, —CH$_2$—CH$_2$—OH), 4.51 (t, —OH), 4.95 (s, 2H Ar—CH$_2$—N), 5.49 (s, 2H, N—CH$_2$—O), 7.01 (d, 1H), 7.06-7.11 (m, 4H), 7.37-7.41 (m, 1H), 7.52-7.56 (m, 1H), 7.71 (d, 1H), 7.83 (d, 1H), 7.87 (d, 1H). $^{13}$C NMR (400 MHz, DMSO-d$_6$, ppm): δ=39.2, 48.0, 63.3, 79.9, 113.9, 118.5, 119.4, 122.4, 124.5, 127.7, 128.9, 129.4, 130.5, 131.9, 132.7, 147.2, 152.7. FT-IR (KBr): ν=1230 cm$^{-1}$ (C—O—C asymmetric stretching), 941 cm$^{-1}$ (oxazine-ring mode).

Characterization. The chemical structure of naphthoxazines 2a-c were confirmed by $^1$H, $^{13}$C, and two-dimensional (2D) HSQC on a Bruker Advance III HD 400 MHz NMR spectrometer using DMSO-d6. The relaxation time used for proton NMR integration of resonances was 10 s and an average number of transient scans was 16. The $^{13}$C NMR spectrum was also acquired in DMSO-d$_6$ with an average number of transient scans of 256. The 2D $^1$H-$^{13}$C HSQC NMR was conducted with 1024 points, sweep width 16 ppm in the F2 dimension and 256 data points, 300 ppm sweep width for the F1dimension with a 1.5 s relaxation delay and 256 total scans. Further structural characterization was completed with a Nicolet iS50 FTIR spectrophotometer with a single reflectance ATR detector. Approximately 1-5 mg of naphthoxazine was ground with KBr, and the spectra were collected in the range of 4000-650 cm$^{-1}$ at room temperature. Thermal decomposition was studied using a TA Instruments Q-500 thermal gravimetric analyzer at a heating rate of 5° C./min with a nitrogen flow of 60 mL/min up to 550° C. A TA instruments Q-5000 digital scanning calorimeter (DSC) was utilized at with a heating rate of 5° C./min and a nitrogen flow rate of 60 mL/min. The activation energy was calculated by analyzing samples (2.5±0.5 mg) at different heating rates of 2, 5, 10, 15, and 20° C./min in sealed hermetic aluminum pans.

Whether or not a reactant or product described herein is "bioderived" may be determined by analytical methods. Using radiocarbon and isotope ratio mass spectrometry analysis, the bio-based content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present-day radiocarbon and fossil carbon (containing no radiocarbon), then the pMC value obtained correlates directly to the amount of biomass material present in the sample. Thus, ASTM-D866 may be used to validate that the compositions described herein are and/or are not derived from renewable sources.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A composition compound having a structure according to formula (I)

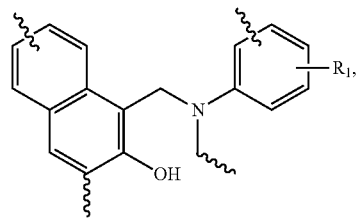

wherein $R_1$ is an alkyl group terminating with a moiety selected from the group consisting of a carboxyl group and a hydroxyl group, and ⌇ comprises a covalent bond.

2. The compound of claim 1, having a structure according to formula (II)

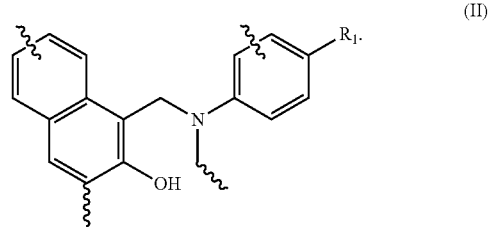

3. The compound of claim 2 having a structure selected from either formula (III) or formula (IV)

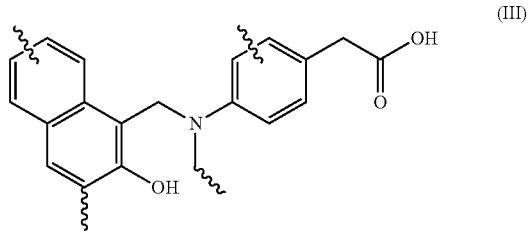

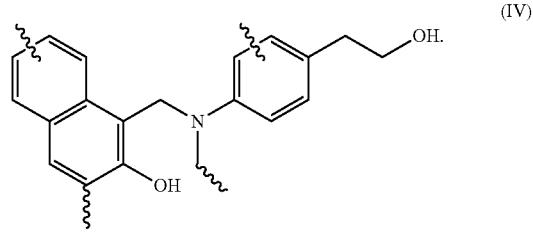

4. The compound of claim 3, wherein the compound is bioderived.

* * * * *